United States Patent
Kawaguchi

(10) Patent No.: US 7,323,719 B2
(45) Date of Patent: Jan. 29, 2008

(54) GROUP III-V NITRIDE SERIES SEMICONDUCTOR SUBSTRATE AND ASSESSMENT METHOD THEREFOR

(75) Inventor: Yusuke Kawaguchi, Tsuchiura (JP)

(73) Assignee: Hitachi Cable, Ltd., Tokyo (JP)

( * ) Notice: Subject to any disclaimer, the term of this patent is extended or adjusted under 35 U.S.C. 154(b) by 25 days.

(21) Appl. No.: 11/033,469

(22) Filed: Jan. 12, 2005

(65) Prior Publication Data
US 2006/0108590 A1    May 25, 2006

(30) Foreign Application Priority Data
Nov. 19, 2004    (JP)    ............... 2004-335913

(51) Int. Cl.
*H01L 27/15*    (2006.01)
(52) U.S. Cl. ................. 257/79; 257/233.001
(58) Field of Classification Search ............... 257/79
See application file for complete search history.

(56) References Cited

U.S. PATENT DOCUMENTS

| | | | | |
|---|---|---|---|---|
| 5,939,735 | A | * | 8/1999 | Tsutsui et al. ............ 257/98 |
| 2002/0185054 | A1 | * | 12/2002 | Xu et al. ............ 117/2 |
| 2003/0030053 | A1 | * | 2/2003 | Kawakami et al. ......... 257/72 |
| 2005/0093101 | A1 | * | 5/2005 | Matsumoto ............ 257/617 |

FOREIGN PATENT DOCUMENTS

JP    11-251253    9/1999

* cited by examiner

*Primary Examiner*—B. William Baumeister
*Assistant Examiner*—Matthew L. Reames
(74) *Attorney, Agent, or Firm*—McGinn IP Law Group, PLLC

(57) ABSTRACT

The group III-V nitride series semiconductor substrate has good-product yield when the band-edge peak light-emission intensity ratio $\alpha = N_1/N_2$ is $\alpha < 1$, where $N_1$ is a band-edge peak light-emission intensity at an arbitrary photoluminescence measurement position on the front side of the substrate, and $N_2$ is a band-edge peak light-emission intensity on the back side of the substrate corresponding to the photoluminescence measurement position.

17 Claims, 3 Drawing Sheets

GROUP III-V NITRIDE SERIES SEMICONDUCTOR SUBSTRATE AND ASSESSMENT METHOD THEREFOR

The present application is based on Japanese patent application No.2004-335913, the entire contents of which are incorporated herein by reference.

BACKGROUND OF THE INVENTION

1. Field of the Invention

The present invention relates to a group III-V nitride series semiconductor substrate and its assessment method. In particular, it relates to a group III-V nitride series semiconductor substrate which allows a compound semiconductor layer to be grown on the substrate in such a way that it is flat and that impurities are uniformly distributed, and to an assessment method which allows quick and convenient assessment as to whether a substrate allows a compound semiconductor layer to be grown on the substrate in such a way that it is flat and that impurities are uniformly distributed.

2. Description of the Related Art

The application of nitride series semiconductor materials to short-wavelength light-emitting devices has been actively made because of wide bandgaps and direct transition type band-to-band transitions. Nitride semiconductor series devices are obtained by performing epitaxial growth on a base substrate, using a vapor phase growth method such as metal organic vapor phase epitaxy (MOVPE), molecular beam epitaxy (MBE), hydride vapor phase epitaxy (HVPE), or the like. In a crystal obtained by these growth methods, however, there exist many crystalline defects. The reason for that is because there is no base substrate of a different kind that matches the lattice constant of a nitride semiconductor. For this reason, a self-standing substrate of the same kind (e.g., GaN self-standing substrate) that matches the lattice constant of a nitride semiconductor has been demanded.

As a crystalline defect reducing technique in a GaN epitaxial growth method, an ELO (epitaxial lateral overgrowth) method has been known (see e.g., Japanese patent application laid-open No.11-251253). ELO is a technique for obtaining a low-dislocation GaN layer by fabricating a mask with stripe openings in abase substrate, and selectively growing GaN initial growth nuclei in the openings. With ELO, a GaN layer is formed in a base substrate, followed by removal of the base substrate, so that a good-quality GaN self-standing substrate is obtained.

Even in the GaN self-standing substrate obtained by the above-mentioned method, however, there have remained the problems with surface flatness of the GaN self-standing substrate, impurity distribution, and warpage of the substrate, etc. For instance, in case of poor surface flatness of the GaN self-standing substrate, poor impurity distribution, or large warpage of the substrate, even if an epitaxial layer for light-emitting devices is grown on that GaN self-standing substrate with MOVPE, the surface flatness of the growth layer and impurity distribution become poor. For this reason, when it is cut into a plurality of chips to fabricate a plurality of light-emitting devices, the light-emission intensity of the individual light-emitting devices is varied widely despite their being formed from the same GaN self-standing substrate. Also, it is difficult to apply lithography to such a substrate, which has a significant effect on good-quality product yield of the devices.

SUMMARY OF THE INVENTION

Accordingly, it is an object of the present invention to provide a group III-V nitride series semiconductor substrate which obviates the above problems in the prior art, and which allows a compound semiconductor layer to be grown on the substrate in such a way that it is flat and that impurities are uniformly distributed, and an assessment method which allows quick and convenient assessment as to whether a substrate allows a compound semiconductor layer to be grown on the substrate in such a way that it is flat and that impurities are uniformly distributed.

The inventor has completed the present invention, based on knowledge found out about the fact that the good-quality product yield of an optical device fabricated on a GaN self-standing substrate depends on the band-edge light-emission peak intensity ratio of the front to back side of the GaN self-standing substrate obtained from photoluminescence (hereinafter, referred to as PL) measurements of the GaN self-standing substrate.

In other words, a group III-V nitride series semiconductor substrate of the present invention is characterized by comprising a self-standing group III-V nitride series semiconductor crystal with both its front and back sides being ground to a mirror finish, and with the band-edge peak light-emission intensity ratio $\alpha=N_1/N_2$ being $\alpha<1$, where $N_1$ is a band-edge peak light-emission intensity at an arbitrary PL measurement position on the front side, and $N_2$ is a band-edge peak light-emission intensity on the back side corresponding to said PL measurement position.

Here, the term "band-edge peak light-emission intensity" refers to PL peak intensity substantially corresponding to band gap energy of a semiconductor crystal in PL spectra emitted from the semiconductor crystal.

The above-mentioned intensity ratio $\alpha$ is preferably $0.1 \leq \alpha \leq 0.5$.

The above-mentioned semiconductor crystal is a hexagonal gallium nitride monocrystalline crystal, the front side of which can be a C-face gallium surface.

The above-mentioned semiconductor crystal can be an n-type impurity-doped conductive crystal. The n-type impurity is exemplified by Si, $O_2$, etc.

Also, an assessment method for a group III-V nitride series semiconductor substrate of the present invention is characterized by assessing a self-standing group III-V nitride series semiconductor substrate as being of good-product yield when the band-edge peak light-emission intensity ratio $\alpha=N_1/N_2$ is $\alpha<1$, where $N_1$ is a band-edge peak light-emission intensity at an arbitrary PL measurement position on the front side of the substrate, and $N_2$ is a band-edge peak light-emission intensity on the back side of the substrate corresponding to said PL measurement position.

The above-mentioned intensity ratio $\alpha$ is preferably $0.1 \leq \alpha \leq 0.5$.

The present invention can provide a group III-V nitride series semiconductor substrate with characteristics required for compound semiconductor growth and the self-standing substrate, by regulating the PL intensity ratio.

The present invention also allows, by regulating the PL intensity ratio, quick and convenient assessment as to whether or not a group III-V nitride series semiconductor substrate allows a compound semiconductor layer to be grown on the substrate in such a way that it is flat and that impurities are uniformly distributed, without constituting a device on the group III-V nitride series semiconductor substrate. Further, since PL measurement is non-destructive and contactless, and a PL measurement apparatus can easily be configured, it can provide an inexpensive, high-efficiency determination method, and is suitable for mass production.

BRIEF DESCRIPTION OF THE DRAWINGS

The preferred embodiments according to the invention will be explained below referring to the drawings, wherein.

DETAILED DESCRIPTION OF THE PREFERRED EMBODIMENTS

Figure 1:
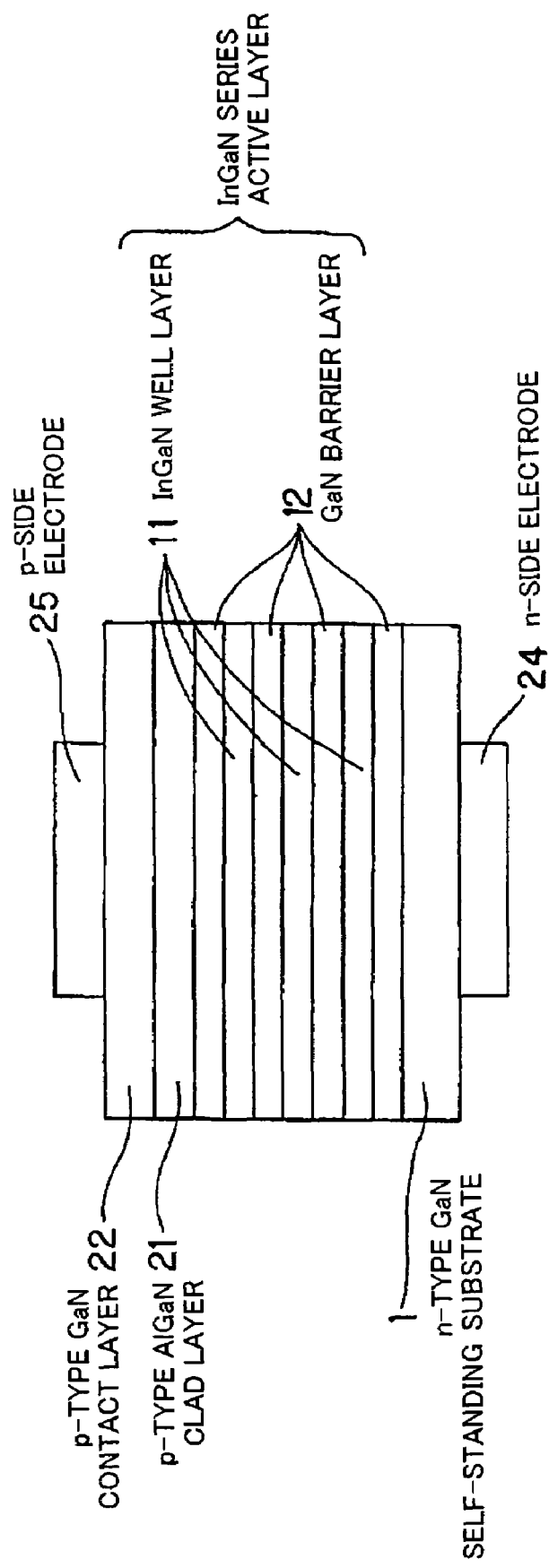
FIG. 1 is a schematic diagram showing LED structure fabricated in each embodiment.

Substrate characteristics on which depends the good-product yield of an optical device formed on a GaN self-standing substrate are exemplified by surface flatness, crystal quality, etc. In order to enhance the good-product yield, the surface flatness, crystal quality, etc. have to be good. However, it is easier to examine the PL intensity ratio than to examine these substrate characteristics to study their corresponding good-product yields.

In the present embodiments, laser light is made incident on a GaN self-standing substrate to observe light-emission intensity from the GaN self-standing substrate, and specifically, to look at the band-edge light-emission peak (peak wavelength 365 nm) PL (photoluminescence) intensity ratio of the front to back side of the GaN self-standing substrate itself.

PL intensity is dependent on a machined damaged layer of a substrate surface, carrier concentration of the substrate and crystal defects. In case machining strains or crystal defects exist in a film, band-edge light-emission intensity becomes high and low. For instance, crystal defects or impurities in the film form energy levels in a bandgap, which results in an increase in carrier density in the crystal. For this reason, if an excited light source is of the same power density, having more carrier density increases PL intensity.

The GaN self-standing substrate is formed by forming a GaN layer on a sapphire substrate with MOVPE, performing ELO to reduce dislocations, and making film thickness large with HVPE. Subsequently, the sapphire substrate is removed to form the GaN self-standing substrate. Thus, the defect density in the GaN self-standing substrate decreases in the growth direction (on the front side). In other words, the crystal quality of the back side is poor compared to that of the front side. Crystal defects, for example, dislocations in which the periodicity of a crystal lattice is mismatched linearly cause stress to the crystal lattice by the mismatch. The difference in this stress between the front and back sides can be the cause of warpage. It is known that such crystal defects produce light-emitting sites in the bandgap. In other words, from the point of view of crystal quality, PL measurement band-edge peak light-emission intensity decreases on the back side of the substrate. However, the number of impurity atoms in a growth initial interface tends to be greater than that of the front surface, and the concentration of the impurity atoms is segregated in the film thickness direction. For this reason, the PL intensity of the substrate back side tends to be greater than that of its front side.

The good-product yield of devices is poor if the band-edge peak light-emission intensity ratio $\alpha = N_1/N_2$ is outside a specified range, where $N_1$ is a band-edge peak light-emission intensity at an arbitrary PL measurement position on the front side of the GaN self-standing substrate, and $N_2$ is a band-edge peak light-emission intensity on the back side of the same substrate corresponding to the PL measurement position of the front side. As seen from results of the embodiments as described later, if $\alpha < 1$, preferably $0.1 \leq \alpha \leq 0.5$, the good-product yield of devices is excellent.

Further, the term "self-standing substrate" refers to a substrate which has such a degree of strength as to allow holding its shape and as not to cause inconvenience in handling. In order to be equipped with such strength, a self-standing substrate preferably has a thickness of 200 μm or more. Also, taking into account ease of cleavage after device formation, etc., the self-standing substrate preferably has a thickness of 1 mm or less. This is because, in case of greater than 1 mm, cleavage is difficult and irregularities are caused in a cleavage surface, which results in the problem, for example that when the self-standing substrate is applied to a semiconductor laser, etc., device characteristics deteriorate due to reflection losses.

Embodiment (Fabrication of the GaN Self-Standing Substrate)

A GaN self-standing substrate was fabricated by the following process.

First, with HVPE, a mixture of GaCl, nitrogen, hydrogen and ammonia gases was blasted on a φ2-inch C-face sapphire substrate heated above 1000° C. to grow a GaN monocrystalline crystal layer by about 330 μm. The frontside of the grown GaN layer was a C-face gallium surface.

Further, the GaN layer was doped with n-type impurities.

Then, in order that the GaN film layer was a self-standing substrate, the sapphire substrate, etc. were roughly cut with large grain sizes (grain sizes 100-600ths) of BN or diamond, and further were carefully ground with small grain sizes (grain sizes 1000ths or more) of BN or diamond to remove the sapphire substrate. This caused the back side of the substrate to be ground to a mirror finish. Then, the front side of the substrate was ground with the above-described method so that the substrate front side was ground to a mirror finish in a similar fashion to the substrate back side. Table 1 shows abrasives used in grinding the self-standing substrate.

TABLE 1

ABRASIVES USED IN FABRICATING THE SELF-STANDING SUBSTARTE

| | Abrasives (grain sizes) |
|---|---|
| Rough cutting | BN, diamond (grain sizes 100-600ths) |
| Mirror finish | Diamond (grain sizes 2000ths or greater) |

In the present embodiments, n-type GaN self-standing substrates Nos.1-9 with nine kinds of features were fabricated, for each of which the relationship between the good-product yield of LED devices and α-values of PL measurements were studied. In order to fabricate the GaN self-standing substrates with respective features, the fabrication was performed changing grinding conditions in the step of grinding the front and back sides of the GaN self-standing substrates. For example, the substrate with poor flatness of the substrate back side (N-face) was a substrate with poor flatness when ground with diamond abrasive grain sizes of 1000ths or less in the mirror finishing step. Similarly, the substrate with poor flatness of the substrate front side was fabricated, grinding it with small diamond abrasive grain sizes in the frontside mirror finishing step. To cause the substrate to have a variation of 10 μm or greater in thickness, the fabrication was performed grinding by making loading non-uniform in the step of grinding either or both of the substrate front and back sides. To fabricate a high defect-density substrate, when, with HVPE, a mixture of GaCl, nitrogen, hydrogen and ammonia gases was blasted on a sapphire substrate heated above 1000° C. to grow a GaN film layer, by changing the ratio of GaCl to ammonia (V/III ratio) and growth temperature, the GaN self-standing substrate with a crystal defect (through dislocation) of $10^8$-$10^9$ cm$^{-2}$ was fabricated.

(Measurements of PL Profiles)

Next, PL profiles of the GaN self-standing substrates with nine kinds of features were measured at room temperature, using a He—Cd laser (wavelength: 325 nm).

In the present measurements, for each substrate with each feature, the GaN band-edge peak light-emission (peak wavelength 365 nm) intensity ratio α=$N_1$/$N_2$ was obtained, where $N_1$ was a GaN band-edge peak light-emission intensity at a PL measurement position on the substrate front side, and $N_2$ was a GaN band-edge peak light-emission intensity on the substrate back side corresponding to the same PL measurement position. Measurements were averaged for the center and four peripheral portions, five positions in total on each substrate. In embodiments 1-9, substantially the same α-values were obtained regardless of PL measurement positions if within the same substrate.

(Fabrication of LED Structure)

FIG. 1 shows LED structure using each of the above-described substrates.

The fabrication of the LED structure used MOVPE. The LED structure was a multiple quantum-well layer such as InGaN, etc. As organic metal raw materials, trimethylgallium (TMG), trimethylaluminum (TMA), trimethylindium (TMI), and bis(cyclopentadienyl)magnesium (Cp$_2$Mg) were used. As gas raw materials, ammonia (NH$_3$) and silane (SiH$_4$) were used. Also, as carrier gases, hydrogen and nitrogen were used.

First, on an n-type GaN self-standing substrate 1 with the above-mentioned nine kinds of features, there was formed an InGaN series active layer 10 having multiple quantum-well (MQW) structure comprising three 3 nm thick In$_{0.15}$Ga$_{0.85}$N well layers 11, and four 10 nm thick GaN barrier layers 12. In this case, growth was suspended after forming each of well layers 11 and barrier layers 12. In its upper portion, a p-type Al$_{0.1}$Ga$_{0.9}$N clad layer 21 and a p-type GaN contact layer 22 were formed in this order. Also, on the back side of the n-type GaN self-standing substrate 1, an n-side electrode 24 comprising Ti/Al was formed. Further, on the p-type GaN contact layer 22, a p-side electrode 25 comprising Ti/Al was formed.

This provided an LED with the structure shown in FIG. 1.

Next, the good-product yield of LED chips within the substrate surface except for a region of a periphery 2 mm of the substrate was assessed. Although there are various factors for determining the good-product yield of LED chips, such as physical factors in a photolithography process, variation of light-emission brightness, variation of light-emission wavelengths, variation of drive voltage, variation of pressure resistance, device life, etc., the good-product yield is defined herein by the integration of them.

Embodiment 1

Substrate No.1 had a backside roughness of 1 μm or larger. The front and back sides of substrate No.1 were mirror-finished. After the front side was ground to a mirror finish, a wet-etching method was applied to the front side for the purpose of obviating machining strains. The wet-etching used phosphoric acid as an etchant. The etching conditions were 240° C. and 2 hours. XRD (X-ray diffraction) measurement verified no machining strains on the front side of substrate No.1. The flatness of the back side of substrate No.1 was poor as surface step measurements showed that it had an average roughness of 1 μm or larger. The flatness of the front side was a few of nm. The α-value of substrate No.1 with the poor backside flatness was 0.01. The examination of the good-product yield of an LED fabricated on substrate No.1 by the above-described process showed an LED device good-product yield of 25%.

Embodiment 2

Substrate No.2 had machining strains on its front side. The growth step was the same as that of embodiment 1. The conditions of the substrate grinding step were the same as those of table 1. Since no wet-etching was performed after the substrate front and back sides were ground to a mirror finish, there were machining strains on the substrate front side due to the grinding. The flatness of the substrate front and back sides was a few of nm.

Figure 2:
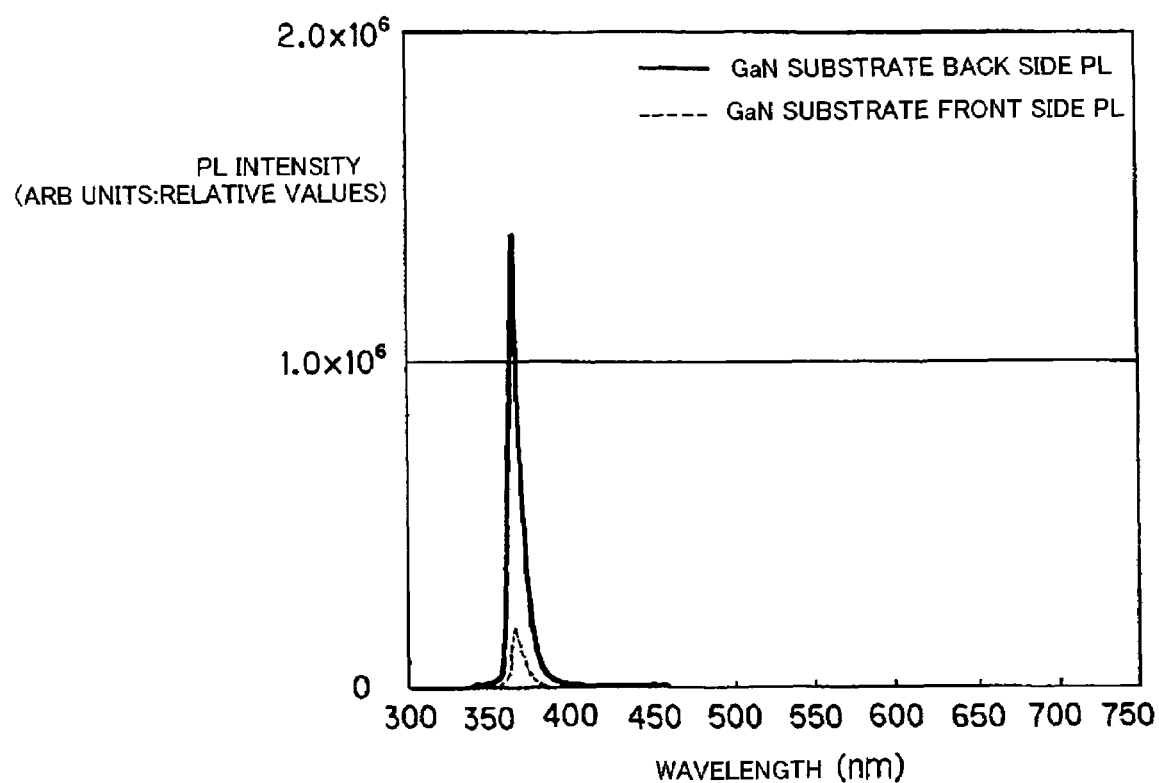
FIG. 2 is a diagram showing PL spectra on the front and back side of a GaN self-standing substrate of embodiment 2.

FIG. 2 shows PL spectra of the front and back sides of the GaN self-standing substrate ground to a mirror finish according to this embodiment. As apparent from FIG. 2, at a wavelength of 365 nm, the backside PL intensity was 1.4×10$^6$ (a.u.), and the frontside PL intensity was 0.18×10$^6$ (a.u.), and the intensity ratio α-value was 0.13.

The examination of the good-product yield of an LED fabricated on substrate No.2 by the above-described process showed an LED device good-product yield of 65%.

Embodiment 3

Substrate No.3 was grown by reducing growth temperature during GaN film growth from 1000° C. to 900° C. The conditions of the substrate growth step except for the growth temperature were the same as those of embodiment 1. The conditions of the substrate grinding step were the same as those of table 1. After the front and back sides of substrate No.3 were ground to a mirror finish, wet-etching treatment was made to substrate No.3. XRD (X-ray diffraction) measurement of the wet-etched front surface showed that dislocations estimated from the XRD were on the order of 1.5 times greater than those of a GaN self-standing substrate fabricated in conventional growth conditions. The flatness of the front and back sides of substrate No.3 was a few of nm. The α-value of substrate No.3 was 0.2. The examination of the good-product yield of an LED fabricated on substrate No.3 by the above-described process showed an LED device good-product yield of 77%.

Embodiment 4

Substrate No.4 had a film thickness difference of 10 μm or greater on average within the surface after its front and back sides were ground to a mirror finish. The conditions of the substrate growth step were the same as those of embodiment 1. The conditions of the substrate grinding step were the same as those of table 1, except that the grinding was performed by changing the balance of machining pressure when the substrate front and back sides were ground to a mirror finish. Since wet-etching treatment was made after the front and back sides were ground to a mirror finish, there were no machining strains on the substrate front side. The flatness of the front and back sides of substrate No.4 was a few of nm. The α-value of substrate No.4 was 0.39. The examination of the good-product yield of an LED fabricated on substrate No.4 by the above-described process showed an LED device good-product yield of 78%.

Embodiment 5

Substrate No.5 had a good substrate frontside flatness of a few of nm. The conditions of the substrate growth step were the same as those of embodiment 1. The conditions of the substrate grinding step were the same as those of table 1. Since wet-etching treatment was made after the substrate front and back sides were ground to a mirror finish, there were no machining strains on the substrate front side. The α-value of substrate No.5 was 0.49. The examination of the good-product yield of an LED fabricated on substrate No.5 by the above-described process showed an LED device good-product yield of 82%.

Embodiment 6

Substrate No.6 was formed with a GaN film grown by reducing the purity of HVPE raw material gases. The conditions of the substrate growth step were the same as those of embodiment 1, except that the purity of the raw material gases was reduced. The conditions of the substrate grinding step were the same as those of table 1. XRD (X-ray diffraction) measurement of substrate No.6 showed that dislocations estimated from the XRD were on the same order as dislocations in prior art. Since wet-etching treatment was made after the substrate front and back sides were ground to a mirror finish, there were no machining strains on the substrate front side. The flatness of the front and back sides of substrate No.6 was a few of nm. The α-value of substrate No.6 was 0.77. The examination of the good-product yield of an LED fabricated on substrate No.6 by the above-described process showed an LED device good-product yield of 49%.

Embodiment 7

Substrate No.7 had a poor substrate frontside flatness of a few hundreds of nm. Although the substrate growth step was the same as that of embodiment 1, the substrate was ground by reducing to 1000ths diamond abrasive grain sizes used in grinding the front surface to a mirror finish in the substrate grinding step. The other conditions of the grinding step were the same as those of table 1. Since wet-etching treatment was made to the substrate front side after it was ground to a mirror finish, there were no machining strains on the substrate front side. The flatness of the substrate backside was a few of nm. The α-value of substrate No.7 was 0.98. The examination of the good-product yield of an LED fabricated on substrate No.7 by the above-described process showed an LED device good-product yield of 47%.

Embodiment 8

Substrate No.8 had a substrate frontside flatness of a few of μm, which was even poorer than that of the substrate of embodiment 7. Although the substrate growth step was the same as that of embodiment 1, the substrate was ground by reducing to 800ths diamond abrasive grain sizes used in grinding the front surface to a mirror finish in the substrate grinding step. The other conditions of the grinding step were the same as those of table 1. Since wet-etching treatment was made to the substrate front side after it was ground to a mirror finish, there were no machining strains on the substrate front side. The α-value of substrate No.8 was 1.05. The examination of the good-product yield of an LED fabricated on substrate No.8 by the above-described process showed an LED device good-product yield of 10%.

Embodiment 9

Substrate No.9 had grinding flaws left on the substrate front side. An AFM (atomic force microscope) observed many scratches of the order of 3 nm in depth present on the front side of substrate No.9 ground to a mirror finish. In this embodiment, wet-etching time subsequent to mirror finishing was 1 hour, which was made shorter than that of embodiment 1. The other conditions of the substrate growth step and the grinding step were the same as those of embodiment 1. The α-value of substrate No.9 was 1.25. The examination of the good-product yield of an LED fabricated on substrate No.9 by the above-described process showed an LED device good-product yield of 10%.

Figure 3:
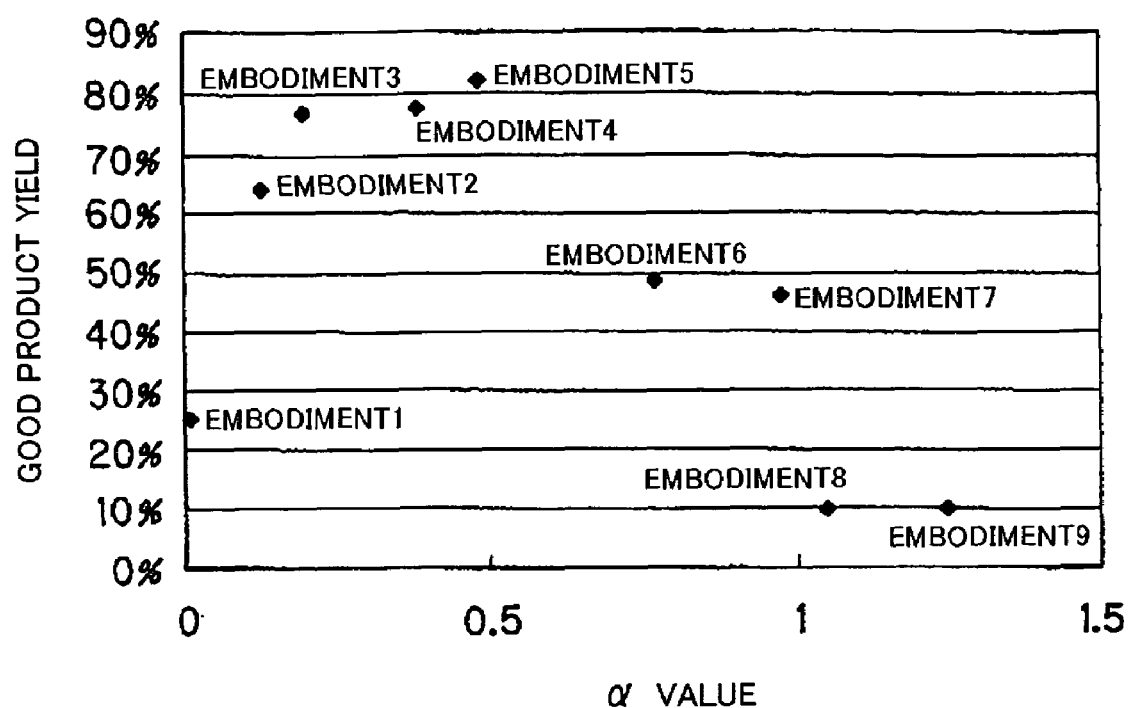
FIG. 3 is a graph showing the correlation between PL $\alpha$ values and LED good-product yields, regarding embodiments 1-9.

FIG. 3 shows the correlation between PL α values and LED good-product yields, regarding embodiments 1-9. Despite many factors on which depends the good-product yield of LED chips, FIG. 3 shows the good correlation between it and the PL α values, and has verified that, in case α exceeds 1, the good-product yield of LED chips falls enormously. It has been found that, in order to obtain the high good-product yield of LED chips, it is desirable that a is in the range of $0.1 \leq \alpha \leq 0.5$.

Although the invention has been described with respect to the specific embodiments for complete and clear disclosure, the appended claims are not to be thus limited but are to be construed as embodying all modifications and alternative constructions that may occur to one skilled in the art which fairly fall within the basic teaching herein set forth.

What is claimed is:

1. A group III-V nitride series semiconductor substrate, comprising:
    a self-standing group III-V nitride series semiconductor crystal with both its front and back sides being ground to a mirror finish, and with the band-edge peak light-emission intensity ratio $\alpha = N_1/N_2$ being a $\alpha<1$, where $N_1$ is a band-edge peak light-emission intensity at an arbitrary photoluminescence measurement position on the front side, and $N_2$ is a band-edge peak light-emission intensity on the back side corresponding to said photoluminescence measurement position,
    wherein said semiconductor crystal comprises a hexagonal gallium nitride monocrystalline crystal, the front side of which comprises a C-face gallium surface.

2. The group III-V nitride series semiconductor substrate according to claim 1, wherein said intensity ratio α is $0.1 \leq \alpha \leq 0.5$.

3. The group III-V nitride series semiconductor substrate according to claim 1, wherein said semiconductor crystal comprises an n-type impurity-doped conductive crystal.

4. The group III-V nitride series semiconductor substrate according to claim 1, wherein the band-edge peak light-emission intensity comprises a photoluminescence peak intensity corresponding to bandgap energy of the self-standing group III-V nitride series semiconductor crystal.

5. The group III-V nitride series semiconductor substrate according to claim 1, wherein the band-edge peak light-emission includes a peak at about 365 nm.

6. The group III-V nitride series semiconductor substrate according to claim 1, wherein the band-edge peak light-emission intensity is dependent on a machined damaged layer of a substrate surface.

7. The group III-V nitride series semiconductor substrate according to claim 1, wherein the band-edge peak light-emission intensity is dependent on a carrier concentration of a substrate.

8. The group III-V nitride series semiconductor substrate according to claim 1, wherein the band-edge peak light-emission intensity is dependent on defects on the self-standing group III-V nitride series semiconductor crystal.

9. The group III-V nitride series semiconductor substrate according to claim 1, wherein the band-edge peak light-emission intensity decreases on the back-side.

10. The group III-V nitride series semiconductor substrate according to claim 1, wherein a number of impurity atoms is greater on the back side than the front side.

11. The group III-V nitride series semiconductor substrate according to claim 1, further comprising an electrode disposed on the self-standing group III-V nitride series semiconductor crystal.

12. The group III-V nitride series semiconductor substrate according to claim 1, wherein the back side comprises a surface roughness of about 1 μm or larger.

13. The group III-V nitride series semiconductor substrate according to claim 5, wherein the band-edge peak light-emission intensity of the back side is about $1.4 \times 10^6$.

14. The group III-V nitride series semiconductor substrate according to claim 13, wherein the band-edge peak light-emission intensity of the front side is about $0.18 \times 10^6$.

15. The group III-V nitride series semiconductor substrate according to claim 1, wherein $\alpha$ is about 0.13-0.39.

16. The group III-V nitride series semiconductor substrate according to claim 1, wherein $\alpha$ is about 0.49.

17. The group III-V nitride series semiconductor substrate according to claim 1, wherein $\alpha$ is about 0.77-0.98.

* * * * *